United States Patent [19]

Mina et al.

[11] Patent Number: 4,847,434

[45] Date of Patent: Jul. 11, 1989

[54] BIPHENOL PROCESS

[75] Inventors: George L. Mina, Orangeburg, S.C.;
Dixie E. Goins, Baton Rouge, La.;
John S. Gramling, Orangeburg, S.C.

[73] Assignee: Ethyl Corporation, Richmond, Va.

[21] Appl. No.: 146,428

[22] Filed: Jan. 21, 1988

[51] Int. Cl.$^4$ .............................................. C07C 39/16
[52] U.S. Cl. .................................................. 568/730
[58] Field of Search ....................... 568/730, 722, 803

[56] References Cited

U.S. PATENT DOCUMENTS 4,086,253  4/1978  Hopper et al. ...................... 568/730
4,380,676  4/1983  Rasberger et al. ................. 568/730

Primary Examiner—Werren B. Lone
Attorney, Agent, or Firm—J. D. Odenweller

[57] ABSTRACT

Phenols, e.g. 2,6-di-tert-butylphenol, are coupled to form biphenols, e.g. 4,4'-bis(2,6-di-tert-butylphenol), by reaction with aqueous hydrogen peroxide under basic conditions in the presence of a phase transfer agent.

10 Claims, No Drawings

BIPHENOL PROCESS

BACKGROUND

Biphenols are very useful chemicals. Biphenol itself can be used in the manufacture of polyesters and polyurethanes. Ethanox®712 Antioxidant (a product of Ethyl Corporation) is the compound 4,4'-bis(2,6-di-tert-butylphenol) and is a very effective antioxidant especially in polymer compositions.

A number of procedures for making biphenols have been reported. Zaweski, U.S. Pat. No. 3,562,338, describes a process for making 4,4'-bis(2,6-di-substituted phenols) by the air oxidation of one mole of 2,6-di-substituted phenol to the corresponding diphenoquinone using an alkali metal hydroxide catalyst followed by reaction with an additional one mole of 2,6-di-substituted phenol in the absence of oxygen to form a 4,4'-bis(2,-6-di-substituted phenol) by an oxidation-reduction reaction.

Zaweski U.S. Pat. No. 3,562,338 also describes a process in which a 2,6-di-alkylphenol is oxidized with air in the presence of a base until one-half of the phenol is converted to the corresponding diphenoquinone. The remaining phenol is unchanged. Air is discontinued and the mixture is heated to convert the entire reaction mixture to 4,4'-bis(2,6-di-alklyphenol).

Hay U.S. Pat. No. 3,631,208 is similar to Zaweski but prefers trimethylamine, heterocyclic amines, metal alkoxides, metal phenoxides or carboxylic acids as the oxidation catalyst.

Reichle U.S. Pat. No. 4,238,627 describes a process similar to that of Zaweski in which the amount of air used to oxidize the 2,6-dialkylphenol is limited to the stoichiometric amount required to convert the phenol to a biphenol.

Strom U.S. Pat. No. 4,410,736 is a modification of the Hay process conducted in a lower alkanol.

Kirshner U.S. Pat. No. 4,447,656 describes a process of catalytically dehydrogenating 2,6-di-tert-butylphenol to the corresponding 4,4'-diphenoquinone and then hydrogenating the diphenoquinone to a 4,4'-biphenol.

Strom U.S. Pat. No. 4,482,754 describes a continuous process of converting 2,6-dialkylphenols to biphenols by reaction with oxygen in the presence of an oxidation catalyst to form the corresponding diphenoquinone followed by reaction with more 2,6-dialkylphenol to form a biphenol.

Makato et al. U.S. Pat. No. 4,564,713 teach a process of dimerizing alkylphenols in an aqueous system containing a surfactant using a copper compound and a basic boron compound as a catalyst.

SUMMARY OF THE INVENTION

It has now been discovered that biphenols can be made in a single reaction by reacting a phenol having at least one hydrogen at an ortho- or para-position with an amount of hydrogen peroxide which will convert the phenols to biphenols without resulting in undesirable amounts of the highly colored diphenoquinone in the final product.

DESCRIPTION OF THE PREFERRED EMBODIMENTS

A preferred embodiment of the invention is a process for making a biphenol, said process comprising reacting a phenol, having at least one position ortho or para to the phenolic hydroxyl group unsubstituted except for hydrogen, with aqueous hydrogen peroxide to cause the direct coupling of one phenolic molecule to a different phenolic molecule through an ortho-ortho, para-para or ortho-para direct bond to form a biphenol.

The process is applicable to any phenol which is capable of forming a biphenol. These phenols are unsubstituted except for hydrogen at at least one ortho- or para-position. They can be represented by the formula:

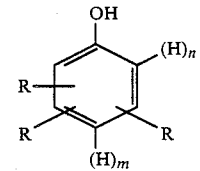

wherein each R is independently selected from hydrogen, halogen, $C_{1-6}$ alkoxy, $C_{1-12}$ alkyl, $C_{5-8}$ cycloalkyl, $C_{6-12}$ aryl and $C_{7-12}$ aralkyl, m and n are 0 or 1 and m+n=1 or 2.

Representative examples of these phenols are phenol, ortho-methylphenol, 2,4-di-methylphenol, 2,6-dimethylphenol, 2-tert-butylphenol, 2-methyl-6-tert-hexylphenol, 2,6-di-cyclopentylphenol, 2-methyl-6-cyclohexylphenol, 2-phenylphenol, 2,4-di-phenylphenol, 2-methyl-6-benzylphenol, 2(α-methylbenzyl)4-methylphenol, 2-methyl-4-chlorophenol, 2,4-di-bromophenol, 2,4-dimethoxyphenol and the like.

In a more preferred embodiment the phenols have substituents other than hydrogen at the 2,6- or 2,4-positions. These can be represented by 2,4-di-tert-butylphenol, 2-tert-butyl-6-chlorophenol, 2-methyl-6-cyclohexylphenol, 2-(α-methylbenzyl)4-methylphenol, 2,6-di(α-methylbenzyl)phenol, 2,6-dichlorophenol, 2,6-di-bromophenol, 2-tert-butyl-4-methoxyphenol, 2,6-di-isopropylphenol, 2,6-di-sec-butylphenol, 2,6-di-tert-pentylphenol and the like.

In a highly preferred embodiment the R substituents in the 2,4- or 2,6-positions are alkyls containing 1-12 carbon atoms. In a still more preferred embodiment the phenol starting material is a 2,6-di-alkylphenol and especially a 2,6-di-tertalkylphenol. The most preferred phenol is 2,6-di-tert-butylphenol.

The aqueous hydrogen peroxide can have almost any concentration from about 10 to 90 weight percent or higher. A preferred concentration is about 35-75 weight percent and more preferably 50-70 weight percent.

The amount of hydrogen peroxide should be an amount that will convert substantially all of the phenol to a biphenol but which does not cause an excessive amount of the highly colored diphenoquinone in the final product. The stoichiometric amount required to do this is 0.5 moles of $H_2O_2$ per mole of phenol according to the following equation:

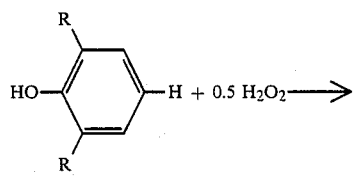

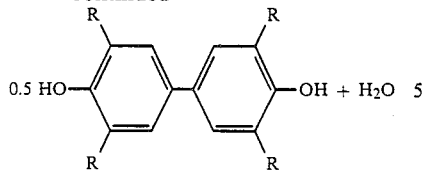

$$0.5 \text{ HO} \underset{R}{\overset{R}{\longleftarrow}} \underset{R}{\overset{R}{\longleftarrow}} \text{OH} + \text{H}_2\text{O}$$

A stoichiometric excess is generally used until the presence of diphenoquinone is observed in the final product as shown by its dark red to violet color. Preferably the product is water white to slightly yellow. A useful range in which to experiment is about 0.5–1.5 moles of hydrogen peroxide per mole of phenol, more preferably 0.6–1.0 moles and most preferably about 0.6–0.75 moles of hydrogen peroxide per mole of initial phenol.

The reaction temperature should be high enough to cause the formation of biphenol but not so high as to cause extensive decomposition. A useful temperature range is about 100°–300° C. and preferably 150°–200° C. and most preferably about 175°–200° C. It is not necessary to conduct the entire reaction in the above temperature range. The initial portion of the reaction can be conducted at a lower temperature of, for example, 50°–150° C., more preferably 75°–150° C. In this lower temperature range, some of the phenol may be oxidized all the way to form a diphenoquinone, but as long as the amount of hydrogen peroxide is held near the optimum amount, there will remain unreacted phenol in the reaction mixture. On continued reaction, the unreacted phenol and diphenoquinone will react with each other to form a biphenol. This latter reaction is preferably conducted at a higher temperature, e.g. 150°–250° C. Hence, the overall temperature range is about 50°–300° C. The reaction should be conducted in a sealed autoclave to prevent vaporization of the reactants at the higher end of the temperature range.

The reaction is preferably conducted under basic conditions. Both organic and inorganic bases can be used. Suitable organic bases include trimethylamine, dimethylamine, triethylamine, butyldimethylamine, pyridine and the like. When using an amine it may be necessary to use additional hydrogen peroxide since part may be consumed converting the amine to an amine oxide or hydroxylamine.

The preferred basic additive is an alkali metal base such as an alkali metal oxide, hydroxide, alkoxide, aryloxide or carbonate. Examples of these are sodium hydroxide, sodium carbonate, sodium oxide, potassium oxide, potassium hydroxide, potassium carbonate, sodium isopropoxide, sodium tert-butoxide, potassium isopropoxide, potassium tert-butoxide, sodium phenoxide and the like including mixtures thereof. The preferred bases are alkali metal hydroxides, especially potassium hydroxide.

The amount of base should by a catalytic amount. This means a small amount but sufficient to cause the reaction to proceed. A useful range in which to operate is about 0.01–0.3 moles of base per mole of phenolic starting material. A preferred range is about 0.03–0.25 moles of base per mole of phenolic and more preferably about 0.05–0.2 moles of base per mole of phenolic.

The reaction rate is substantially increased by including a phase transfer agent. These can be the conventional phase transfer agents such as the quaternary ammonium halides and crown ethers or a co-solvent such as an alkanol, glycol, polyglycol and the like. Examples of conventional phase transfer agents are tetramethylammonium chloride, tetraethylammonium bromide, tributylmethylammonium chloride, tetrabutylammonium bromide and the like. Examples of co-solvent phase transfer agents are isoproponal, tert-butanol, ethylene glycol, diethylene glycol, triethylene glycol, polyethylene glycol, (mw 600) and the like.

The preferred phase transfer agents are the quaternary ammonium halides, especially tetra-alkyl ammonium halides such as tri-butyl methyl ammonium chloride.

The amount of phase transfer agent should be an amount which will cause the reaction to proceed at an increased rate. A useful range in which to experiment is about 0.01–5.0 weight percent based on the quantity of aqueous hydrogen peroxide in the mixture. A preferred amount is about 0.1–3.0 weight percent and more preferably about 0.5–2 weight percent.

The process is readily conducted by placing the phenolic reactant, aqueous hydrogen peroxide, base and phase transfer agent, if used, in a pressure resistant autoclave and stirring the mixture while heating to reaction temperature. The reaction time will depend on the temperature but at the preferred 150°–250° C. will be substantially complete in about 1–12 hours.

The following example shows the manner in which the process can be conducted.

EXAMPLE

In an autoclave fitted with a turbine-type agitator was placed 103.2 grams (0.5 moles) of 2,6-di-tert-butylphenol, 4 grams of 50 weight percent aqueous KOH (0.036 moles) and 1 ml of 50 weight percent aqueous tri-butyl methyl ammonium chloride. The autoclave was sealed and heated while stirring to 150° C. Then, 40 ml of 50 weight percent hydrogen peroxide was added from a head tank and the temperature rose rapidly to 200° C. at 300 psig. After 5 minutes a sample was taken which analyzed by Gas Chromatography at 10 area percent 4,4'-bis(2,6-di-tert-butylphenol) and 90 area percent 2,6-di-tert-butylphenol. Stirring was continued for one hour at 200° C. at which time the autoclave was discharged and the solid product which formed was slurried in water, filtered, water washed and dried to give 99.5 grams of a solid product analyzing 90 percent 4,4'-bis(2,6-di-tert-butylphnol) and 10 percent 2,6-di-tert-butylphenol. The product was re-crystallized from isopropanol to give 99 percent pure 4,4'-bis(2,6-di-tert-butylphenol), m.p. 185°–186° C.

We claim:

1. A process for making a 4,4'-bis(2,6-di-alkylphenol), said process comprising reacting a 2,6-dialkylphenol with aqueous hydrogen peroxide in the presence of an alkali metal base and a phase transfer catalyst.

2. A process of claim 1, wherein said phase transfer agent is a quaternary ammonium halide.

3. A process of claim 1 conducted in the presence of an alkali metal hydroxide.

4. A process of claim 3 wherein said phase transfer agent is a quaternary ammonium halide.

5. A process of claim 4 wherein at least one of the alkyl substituents is a tert-alkyl.

6. A process of claim 5 wherein said dialkylphenol is 2,6-di-tert-butylphenol.

7. A process of claim 6 wherein the amount of hydrogen peroxide is at least 0.5 moles per mole of 2,6-di-tert-butylphenol but less than the amount that will result in any substantial amount of 3,3',5,5'-tetra-tert-butyl-4,4'-diphenoquinone in the final reaction mixture.

8. A process of claim 7 conducted at least part of the reaction period at a temperature of 150°–250° C.

9. A process of claim 8 wherein said alkali metal hydroxide is potassium hydroxide.

10. A process of claim 9 wherein said quaternary ammonium halide is a tetra-lower alkyl ammonium chloride.

* * * * *